United States Patent [19]

Lewis, Jr.

[11] Patent Number: 4,553,970

[45] Date of Patent: Nov. 19, 1985

[54] COLLAPSIBLE MOLDED CONTAINER

[75] Inventor: Dan Lewis, Jr., Lafayette, Calif.

[73] Assignee: Miles Laboratories, Inc., Elkhart, Ind.

[21] Appl. No.: 566,253

[22] Filed: Dec. 28, 1983

[51] Int. Cl.$^4$ .............................................. A61M 5/00
[52] U.S. Cl. ..................................... 604/408; 222/107
[58] Field of Search ........................ 604/408, 403, 410; 222/107, 92, 105; 150/45, 0.5, DIG. 1; 383/119

[56] References Cited

U.S. PATENT DOCUMENTS

| | | | |
|---|---|---|---|
| 3,215,299 | 11/1965 | Coanda et al. | 215/253 X |
| 3,810,503 | 5/1974 | Lewis, Jr. et al. | 383/96 |
| 3,921,630 | 11/1975 | McPhee | 222/107 X |
| 3,926,341 | 12/1975 | Lhoest | 222/107 X |
| 4,049,033 | 9/1977 | Ralston, Jr. | 222/107 X |
| 4,090,541 | 5/1978 | Cammarata et al. | 222/107 X |
| 4,100,953 | 7/1978 | Miller | 222/107 |
| 4,232,721 | 11/1980 | Martin et al. | 222/107 X |
| 4,244,409 | 1/1981 | Wilson et al. | 222/107 X |

*Primary Examiner*—Stephen C. Pellegrino

*Attorney, Agent, or Firm*—David J. Aston; James A. Giblin

[57] ABSTRACT

A molded, collapsible container for intravenous solutions characterized by a controlled collapse along major sidewall portions. The container comprises the shoulder portion having a rigid neck; a hanger portion at an end of the container opposite from the neck; a pair of opposed minor sidewall portions, defined by relatively sharply angled edges; and major sidewall portions extending between the minor sidewall portions which collapse upon each other, while the minor sidewall portions remain in relatively fixed relationship and hold the container apart near the edges of the container. The container may also be provided with intermediate sidewall portions angled relative to the major and minor sidewall portions, which serve to provide a larger fluid capacity to the container. A waist portion is also provided which is relatively smaller circumferentially, compared to the rest of the container. The waist portion provides a rigidifying area which allows air to flow across the width of the container and down along its sides adjacent the minor sidewall portions.

6 Claims, 14 Drawing Figures

COLLAPSIBLE MOLDED CONTAINER

BACKGROUND OF THE INVENTION

1. Field of the Invention

The present invention relates to molded plastic containers, and, more particularly, to a collapsible container for administration of parenteral solutions without the introduction of ambient air to the container.

2. Prior Art

Wilson et al., in U.S. Pat, No. 4,244,409, issued Jan. 13, 1981, disclose a blow molded collapsible container for medical fluids which is characterized by a body section of a flat tubular configuration, a uniform taper to a bottom hanger section, and weakened shoulder portions which form pleated sections.

Martin et al., in U.S. Pat. No. 4,232,721, issued Nov. 11, 1980, disclose a molded collapsible container comprising lines of weakness in shoulder gusset portions to improve collapse and a flat sealed end.

Miller, in U.S. No. 4,100,953, issued July 18, 1978, discloses a collapsible container having rigid ends connected by a flexible tubular wall.

Cammarata et al., in U.S. Pat. No. 4,090,541, issued May 23, 1978, and Ralston, in U.S. Pat. No. 4,049,033, issued Sept. 20, 1977, disclose a flexible collapsible container having lines of folding weakness formed by thinner portions of the container wall along the edges of the shoulder.

McPhee, in U.S. Pat. No. 3,921,630, issued Nov. 25, 1975, discloses a collapsible container which is generally oval in cross section and which collapses through concave collapse of the major sidewalls.

Lewis et al., in U.S. Pat. No. 3,810,503, issued May 14, 1974, disclose a collapsible container wherein the sidewalls are pleated in a V-shape.

Coanda et al., in U.S. Pat. No. 3,215,299, disclose a collapsible container with a hinged hanger.

In general, problems which have been associated with the prior art include weight, and inherent cost; clarity; and collapsibility which is predictably constant, does not require a large volume of internal sterile air, and provides an easily readable meniscus.

SUMMARY OF THE INVENTION

In order to solve the foregoing general problems associated with collapsible containers for medical solutions, a container is provided which is formed from a semi-flexible plastic material, which gives the container the ability to collapse evenly and rapidly, and which comprises a shoulder portion; a hanger portion; and a continuous, multifacted semi-flexible sidewall position extending therebetween. The shoulder portion contains a neck portion and a closure into which an intravenous administration set or the like may be inserted. The hanger portion comprises a loop of rigid plastic into which an extension from an i.v. stand may be inserted when the container is hung for administration of its contents. The multifaceted, semi-flexible sidewall comprises a number of distinct portions which cooperate together to provide an improved container, A first pair of opposed minor sidewall portions extend the length of the sidewall portion and are defined each by a pair of generally convergent longitudinal fold lines which have an acute radius of curvature. The minor sidewalls thus form a relatively narrow band around the container and impart to the container a rigidity which prevents total collapse of the container from convergent movement of the minor sidewalls and, in addition, from total convergent movement of major sidewall portions. A second pair of sidewall portions comprises a pair of major sidewall portions, which, during container collapse, assume a concave configuration toward each other, and tend to merge in the center of the container as the container collapses. These portions cooperate with the rigid minor sidewalls to provide two parallel columns of air which promote even fluid drainage. Intermediate sidewall portions, also defined by fold lines, connect the minor sidewall portion and the major sidewall portion in a tapered configuration broadening towards the shoulder portion to provide a uniformly gradual enlargement of container volume towards the shoulder portion. This serves to insure that container collapse proceeds progressively towards the shoulder portion without intermediate areas of collapse which would tend to trap fluid within the container.

A waist portion also extends circumferentially about the sidewall portion in an area closer to the hanger portion than the shoulder portion. When the container is filled with solution, an ullage void is provided in the hanger portion of the container when the container is hung in a position for administration. The ullage void is contained in an outwardly flared base chamber portion of the container. This base chamber is sized to be disposed immediately above the waist portion. The waist portion is constructed of material which is thicker than the material in the sidewall portion immediately above and below the waist portion, and the waist portion is generally smaller in a cross-sectional area than either the base chamber portion immediately above it or the sidewall portion immediately below it. Thus, the waist portion retains a relatively rigid configuration during container collapse and provides a means of air communication between the two longitudinal air columns.

DESCRIPTION OF THE PREFERRED EMBODIMENT

Figure 1:
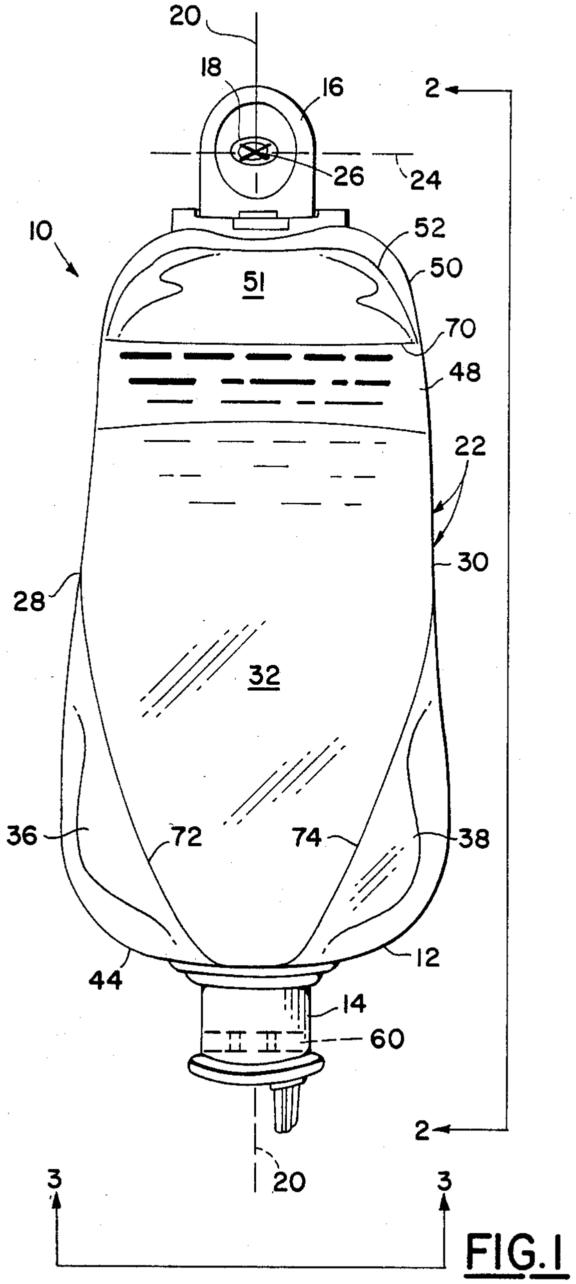
FIG. 1 is a front view of a filled container according to the present invention.

Referring now to FIG. 1, there is shown in general a container 10 having a shoulder portion 12 in which is formed a rigid neck portion 14 for bearing an inner and outer closure and entry ports from which the fluid may be withdrawn.

Disposed at the opposite end of the container 10 from the neck portion 14 is a hanger portion 16. The hanger portion at 16 defines an aperture 18 into which an arm of a standard i.v. stand may be inserted when the container is hung for the administration of its contents. When the container is hung, a longitudinal axis 20 may be said to extend generally vertically. The longitudinal axis 20 extends through the center of the opening in the neck portion 14, through the center of a circle defined by the aperture 18, and generally through the center of the container 10, the container being essentially bilaterally symmetrical about the longitudinal axis.

A continuous, multifacted, semi-flexible sidewall 22 may be said in general to extend between the neck portion 14 and the hanger portion 16. The continuous sidewall portion 22 comprises a number of smaller sidewall portions which are defined by and interconnected by lines of curvature which are relatively sharp compared to the curvature of the various sidewall portions and are referred to herein as "fold lines".

Figure 2:
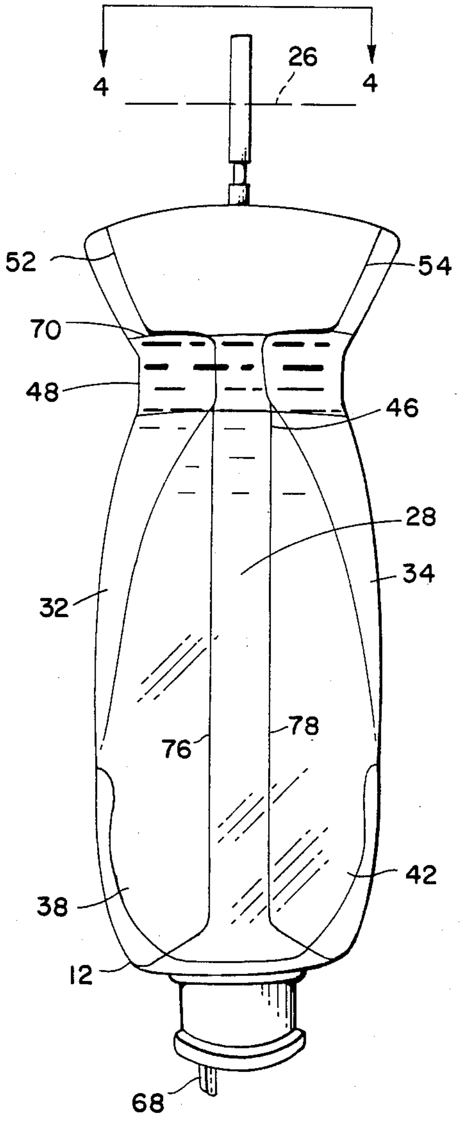
FIG. 2 is a side view of the container of FIG. 1.
Figure 3:
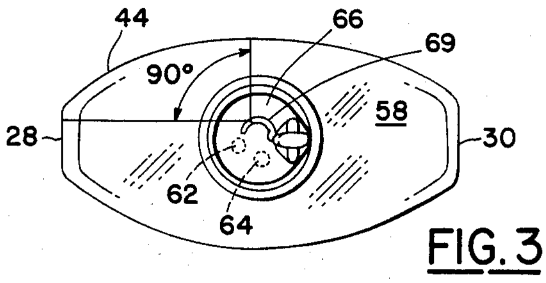
FIG. 3 is a top view of the container of FIG. 1.

For convenient reference to the various sidewall portions, a major axis 24 and a minor axis 26 may be constructed in intersecting perpendicular relationship to the longitudinal axis 20, major axis 24 being the longer of the two axes. A pair of opposed minor sidewall portions 28, 30 are disposed at opposite ends of the major axis. The minor sidewall portions extend continuously through the hanger portion 16 and the neck portion 14, without interruption by fold lines, to provide, in essence, a band around the container which controls collapse as described below. A pair of major sidewall portions 32, 34 are located at opposite ends of the minor axis 26 and extend generally from the neck portion 14 to the hanger portion 16. The major sidewall portions 32, 34 are relatively three to four times larger in area than the minor sidewall portions 28, 30 and tend to collapse towards each other during container drainage while the minor sidewall portions remain in a relatively fixed position. Intermediate sidewall portions 36, 38, 40, 42 serve to connect the minor sidewall portions 28, 30 to the major sidewall portions 32, 34. Each intermediate sidewall portion is essentially identical and is generally in the shape of an acute triangle having a radius of curvature at its base support line 44, of approximately 90°, as shown in FIG. 3. As shown in FIG. 2, the apex 46 of the acute triangle merges with a minor sidewall portion, a major sidewall portion and a waist portion 48.

The waist portion 48 is generally in the form of a rectangular band extending circumferentially about the container in a plane perpendicular to the plane defined by the major and minor axes. This portion of the continuous, multifaceted sidewall 22 is slightly thicker than the plastic material in the adjacent portions of the container so that this portion does not collapse or deform appreciably during container drainage.

Figure 4:
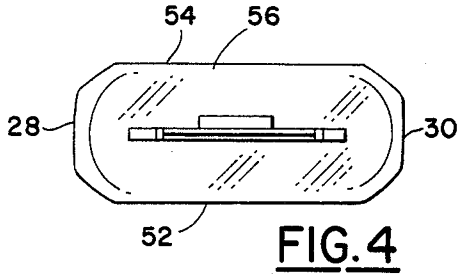
FIG. 4 is a bottom view of the container of FIG. 1.

A base chamber portion 50 is disposed between the waist portion 48 and the hanger portion 16. This portion is normally filled with sterile air and/or sterile liquid when the container is hung. In this portion, the minor sidewalls 28, 30 are broadened outwardly along the minor axis 26 and the major sidewall portions 32, 34 are curved concavely outwardly along the minor axis 26. Arcuate fold areas 52, 54 extend generally along the longitudinal and major axes to separate the sidewalls from the hanger portion 16 which comprises a rather broad planar base portion 56 in the vicinity of the hanger (FIG. 4). An obliquely angled fold area 70 separates the base chamber 50 from the waist portion 48 to provide an area of controlled collapse. The foregoing arrangement serves to provide a base chamber portion which does collapse inwardly above the waist during container drainage but does not collapse longitudinally or along the major axis, and does not close along the minor axis due to the rigidifying effect of the waist portion 48.

Referring now to FIGS. 2 and 3, the neck portion 14 is centered relative to the shoulder portion 12, which may be seen to further comprise a generally oval surface 58 which extends between the fold lines 44 and merges gradually with the minor sidewall portions 28, 30.

The neck portion 14 is generally cylindrical in shape, extends downwardly and contains therein a circular disc 60 (FIG. 1) affixed thereto. Disc 60 contains a medicament entry port 62 and a spike port 64 as is known in the art. The spike port comprises a thinned section of plastic in said disc surrounded by an annular ring for receiving a rupturing spike in a conventional non-vented administration set. An outer closure 66 is provided to seal the disc 60 from the external environment and preserve the sterility of the openings 62, 64. The outer closure 66 is provided with an easy opening feature 68 in the form of a handle and a scored line tear strip 69. The neck portion 14 is comprised of thicker material than the remainder of the container.

The hanger portion 16 may be either integrally molded with, or affixed to the broad planar surface 56 and is centered relative thereto. The broad planar surface 56 is defined by the fold lines 52, 54 on its longer sides, and merges with the minor sidewall portions 28, 30 as shown in FIG. 4. The minor sidewall portions define a generally circular radius of curvature, in the view of FIG. 1, from their linear parallel side portions to the planar base portion.

Each major sidewall portion 32, 34 may thus be seen to extend from a fold line 52, 54 at its upper end to a fold line 72, 74 at its lower end; be comprised in a base chamber 50 separated by a fold line 70 from the waist portion 48; and separated by intermediate sidewall portions by fold lines as illustrated at 72, 74 of FIG. 1, which converge in a generally parabolic curve towards the neck portion, and which curve outwardly from the waist portion to the shoulder portion.

The fold lines 72, 74 are obliquely angled in the view of FIG. 2 relative to the waist portion 48. Fold lines 76, 78 which separate the minor sidewall portion 28 from the intermediate and major sidewalls, as well as the corresponding fold lines defining minor sidewall portion 30, extend downwardly to form oval surface 58 and upwardly to form the generally planar base 56.

The fold lines 72, 74 serve to define the intermediate sidewalls adjacent thereto and are generally straight in the view of FIG. 2 and in the shape of a half parabola in the front view of FIG. 1. These lines are intended primarily to stabilize the container shape as the major sidewalls change during drainage from convex to flat to concave.

Figure 5:
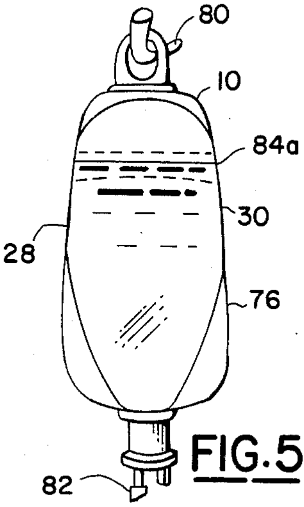
FIG. 5 is a front view of a container according to the present invention which is filled with solution.

Referring now to FIG. 5, there is shown the container 10 of FIG. 1 as it would be normally hung from an i.v. stand with a standard administration set 82, shown in fragmentary view, inserted into opening 64. No air is admitted to the container through the administration set spike. The container is filled with an intravenous solution of a type known in the art, which meniscus is shown at 84*a* as having an upper surface through the waist portion 48, just below fold line 70. Sterile air or the like is contained above the solution level. The ratio of air to solution may vary depending upon the application intended for a particular product, but for a typical one liter size container, between 30 and 100 ml. of air will be contained in the base chamber above the solution.

Figure 8:
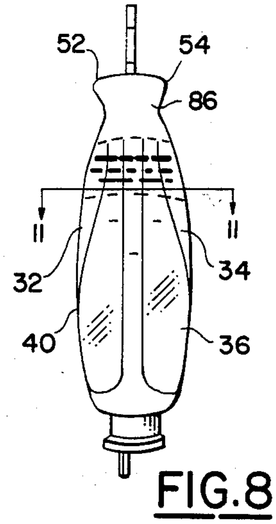
FIG. 8 is a side view of the container of FIG. 5.

As shown in FIG. 8, pressure from the weight of the solution deforms the container by causing outward bulging of the major sidewall portions 32, 34 and the intermediate sidewall portions 36–42. As shown by the side view in FIG. 5, the minor sidewall portions 28, 30 retain their more or less parallel configuration and planar shape. The base chamber above the waist portion 48, indicated generally at 86 in FIG. 8 is bulged slightly outwardly as shown by a more divergent orientation of the sidewall portions 32, 34 in the vicinity of the fold lines 52, 54.

Figure 11:
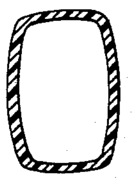
FIG. 11 is a sectional view, taken along line 11—11, of the container of FIG. 8.

As shown in FIG. 11, a cross sectional view of a filled container as shown in FIG. 5, assumes a generally rectangular shape radiused at the corners.

Figure 6:
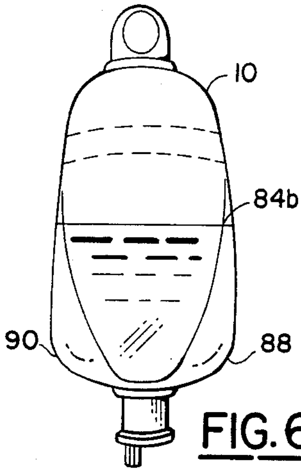
FIG. 6 is a front view of the container of FIG. 5 which is approximately one half full of solution.
Figure 7:
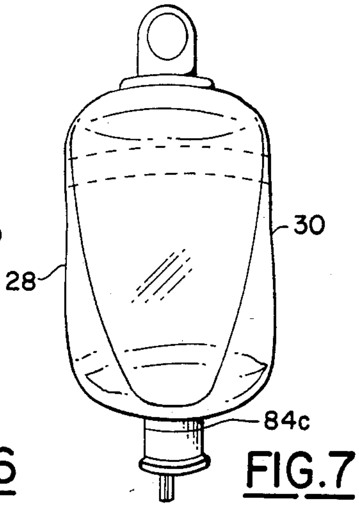
FIG. 7 is a front view of the container of FIG. 5 which is drained of solution.
Figure 9:
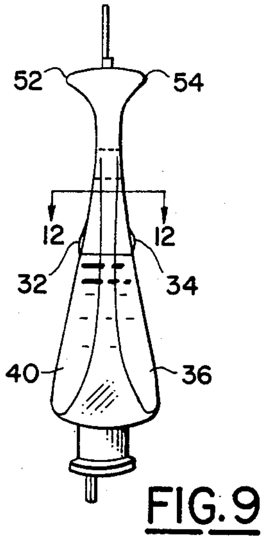
FIG. 9 is a side view of the container of FIG. 6.
Figure 10:
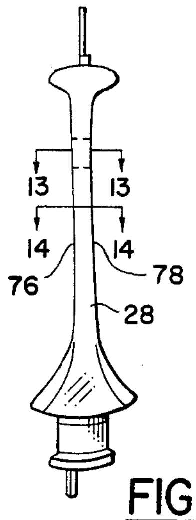
FIG. 10 is a side view of the container of FIG. 7.
Figure 12:
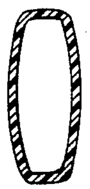
FIG. 12 is a sectional view, taken along line 12—12, of the container of FIG. 9.

Referring now to FIGS. 6, 9, and 12, a general configuration of the container 10 in a partially drained condition, contrasted with that shown in FIGS. 5, 8, and 11, is represented. The meniscus 84*b* represents approximately one third drainage from the container.

In FIG. 6, a noticeable widening of the container along the major axis 24 may be observed in the vicinity of the shoulder portion 12. This accompanies a decreased angle of the radius of curvature of the fold lines 76, 78 in the vicinity of the shoulder portion as represented at 88, 90 of FIG. 6. A concomitant convergence of major sidewalls 32, 34 can be observed in FIG. 9, as these walls no longer extend outwardly past intermediate tapered portions 36, 40. As also shown in FIG. 9, the base chamber, above the waist portion 48, has undergone deformation mostly characterized by a convergence of the major sidewalls 32, 34 in the vicinity of fold lines 52, 54. To summarize, as the minor walls diverge the major walls converge during drainage.

The convergence of the major sidewalls 32, 34 represents a decrease in base chamber volume, as the air as originally sealed in the container migrates below the waist portion to displace the solution from the container as the container collapses. The air in the container as shown in FIG. 9 is thus nearly equal in pressure to the air in the container as shown in FIG. 8, and is still operating to drive the solution from the container. The container portion just below the waist portion 48*a* still shows the slight outward bulging caused by this air pressure, as shown in FIG. 12.

Referring now to FIGS. 7, 10, 13, and 14, a container is shown in a nearly empty condition, contrasted with the container of the preceding FIGS. 5–12. The solution level shown at 84*c* is down to the neck portion 14 of the container 10. The minor sidewalls 28, 30 are now seen in FIG. 7 to be substantially parallel and the major axis 24 is at its maximum length at all points along the longitudinal axis 20. The major sidewall portions 32, 34 and the intermediate sidewall portions 36–42 are at their state of maximum collapse, due to the evacuation of air and fluid from the container. The intermediate sidewall portions 36–42 are, in this condition, substantially coplanar with the major sidewall portions 32, 34, fold lines 72, 74 being substantially unfolded. The flattened major and intermediate sidewall portions between them assume a concave shape along both the longitudinal axis 20 and the major axis 24.

Figure 13:
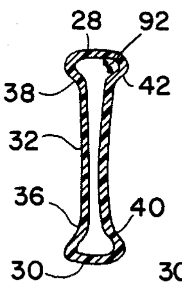
FIG. 13 is a sectional view, taken along line 13—13, of the container of FIG. 10.

FIG. 13 shows a cross sectional view through the waist portion 48 of the container. The minor sidewall portions 28, 30 retain a substantially planar, parallel configuration, with a slight outward bowing across their width in response to the collapse along the minor axis. The central major sidewall portion 32 is slightly concave yet spaced from the corresponding major sidewall of the other side of the container. Small radii of curvature 92 (on the order of O.05 in. to 0.20 in.) between the major and minor sidewalls add dimensional stability and rigidity to the waist portion.

Figure 14:
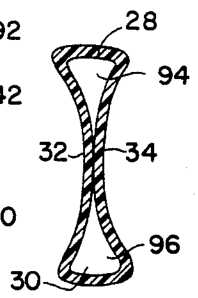
FIG. 14 is a sectional view, taken along line 14—14, of the container of FIG. 10.

Referring now to FIG. 14, a different cross sectional configuration may be observed at various points along the longitudinal axis between the waist portion and the shoulder portion 12. Here the central portions of the major sidewall 32, 34 are in contact along a substantial portion of the major axis. There are, however, two columnar openings 94, 96 adjacent the minor sidewalls 28, 30. These openings 94, 96 extend substantially the entire length of the container from the shoulder portion to the base chamber portion. These columns provide a meniscus which is even and easily read throughout administration of the I.V. solution.

The material of the present container is defined in terms of flexibility by flexural modulus standard ASTM D 790 as a semi-flexible plastic, i.e. 40,000–100,000 psi. This plastic may be PVC, polyethylene, polypropylene, propylene-ethylene copolymers, propyleneethylene-butylene terpolymers, EVA copolymers, or other polymeric materials, such as a blend of styrene-ethylene-butylene-styrene and a polyolefin.

A particular blow-molding process wherein the resultant containers are biaxially oriented involves working of tubular parisons. The parisons are formed from either extruded and cut pipe or from injection molds. The parisons are reheated and stretched-pulled by an external clamp. During the stretch cycle, the parisons are preblown to a circumference which is less than the perimeter of the smallest cross section of the finished container. One to thirty psig air pressure, preferably six to fifteen psig is used in this operation. The preblown parisons are then heat blown into containers in a mold. A blow pin bushing is used to shape the internal diameter and crown dimensions of the neck finish.

Other blow molding processes may also be used.

Thermoformed containers may be made from extruded sheet which is reheated and formed in a second operation into container halves which are then welded together into containers.

The formed containers are inspected and accepted for quality by established standards, then filled, capped, over-capped, sterilized, labeled, inspected, and shipped. During finishing, containers with no hangers are fitted with hangers. Overwraps from high density polyethylene-Vistanex blends, or the polyolefins named above are optional.

In solutions manufacture, the inspected containers are filled with 20% to 94% sterile solution, balance sterile air. Air is expelled from the filled container before sealing to compensate for volumetric shrinkage during sterilization. The volume of air expelled should be equal to or greater than the volumetric shrinkage incurred to provide dimensional stability.

The radii between the shoulder and body (fold line 44), the base chime and the body (fold lines 52, 54), between the major and minor body walls (fold lines 76, 78), and between the intermediate sidewalls and the major sidewalls (fold lines 72, 74) should be small, in the 0.010 inch–0.18 inch range, but preferably in the 0.05 inch–0.09 inch range. These small radii enhance the body collapse along well defined lines.

Numerous alternatives within the scope of the present invention are possible. For instance fold lines may be replaced by grooves or ribs for the intended rigidifying effect, especially with regard to fold lines 72, 74. Containers made in accordance with the foregoing description may be fabricated by a number of known plastic techniques, including blow-molding and thermoforming.

What is claimed is:

1. In a molded collapsible medical solution container of the type intended for delivery of a sterile solution without the introduction of extrernal air, the improvement which comprises:

(a) a neck portion comprising means for emptying said solution from said container, (b) a shoulder portion surrounding said neck portion and having a length and a width, (c) a pair of opposed, collapsing sidewall portions extending along the length of said shoulder portion and in a generally convergent direction from the shoulder portion to a base portion, (d) a pair of opposed, generally parallel, substantially planar minor sidewall portions extending in width between and continuous with said collapsing sidewall portions and having a slight outward bowing across their width in response to collapse of the sidewall portions for preventing, adjacent thereto, mutual and total contact between said collapsing sidewall portions, and for assuring two columnar openings adjacent the minor sidewalls during container collapse, and (e) a rigidifying waist portion extending circumferentially around said collapsing sidewall and minor portions in an area closer to the base portion than the shoulder position for maintaining a generally rectangular configuration during container collapse.

2. The container of claim 1 further comprising intermediate sidewall portions, defined by fold lines, connecting said minor sidewall portions and said major sidewall portions.

3. The container of claim 2 comprising a base chamber portion of said container, between said waist portion and said hanger portion, for containing sterile air.

4. The container of claim 3 wherein said waist portion is smaller in cross sectional area than said base chamber portion, said base chamber portion comprising major sidewalls tapered outwardly from corresponding major sidewall portions in said waist portion.

5. The container of claim 3 wherein said waist portion has a wall thickness greater than wall thickness between said waist portion and said shoulder portion.

6. The container of claim 3 wherein said container, in cross section taken at a point along its length between said shoulder portion and said waist portion, defines major sidewall portions which are concave.

* * * * *